United States Patent [19]

Bouchaudon et al.

[11] 4,362,716

[45] Dec. 7, 1982

[54] DIPEPTIDES, THEIR PREPARATION AND COMPOSITIONS CONTAINING THEM

[75] Inventors: Jean Bouchaudon, Morsang-sur-Orge; Daniel Farge, Thiais; Claude James, Paris, all of France

[73] Assignee: Rhone-Poulenc Industries, France

[21] Appl. No.: 163,877

[22] Filed: Jun. 27, 1980

[30] Foreign Application Priority Data

Jun. 29, 1979 [FR] France ............................ 79 16843

[51] Int. Cl.$^3$ ..................... A61K 37/00; C07C 103/52
[52] U.S. Cl. ............................. 424/177; 260/112.5 R
[58] Field of Search ................. 260/112.5 R; 424/177

[56] References Cited

U.S. PATENT DOCUMENTS 4,311,640  1/1982  Kuroda et al. ............... 260/112.5 R

FOREIGN PATENT DOCUMENTS 11283  5/1980  European Pat. Off. ...... 260/112.5 R
13856  6/1980  European Pat. Off. ...... 260/112.5 R

OTHER PUBLICATIONS

Biochem—and Biophys. Res. Commun. 59, 1974, 1317-1325.
Biochemistry vol. 9, No. 4, 1970, 823-831.
Comptes Rendus Hebdomandaires des Scanies de l'academie α des Sciences Paris, pp. 1320-1304 (1965).
Bulletin de la Societe de Chimie Biologigie 1967, 49, No. 11, pp. 1579-1591.
Agricultural and Biological Chemistry 41, (5) 763-768, 1977.
11th Internat'l Congress of Chemotherapy-19th Interscience Conference on Antimicrobial Agents & Chemotherapy (1979).
Life Sciences 26, 883-888 (1980) "A Shor Lipopeptide, Representative of a New Family of Immunological Adjuvants Devoid of Sugar".
Comptes Rendus de l'Academie des Sciences (Paris), Series D 389, 437-476 (1979) "Properties Immunostimulantes et Adjuvantes d 'un Lipopeptide de Faible Poids Moleculares".

*Primary Examiner*—Delbert R. Phillips
*Attorney, Agent, or Firm*—Stevens, Davis, Miller & Mosher

[57] ABSTRACT

Dipeptides of the formula:

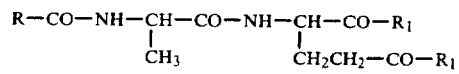

in which R-CO represents a fatty acid residue and the symbols $R_1$, which are identical or different, represent hydroxyl, amino or alkoxy containing 1 to 4 carbon atoms, which is optionally substituted by phenyl or nitrophenyl, it being understood that the alanine is in the L form and the glutamic acid or derivative thereof is in the D form, and their salts are immunological adjuvants and immunostimulants. They may be made using methods known per se in peptide chemistry and may be incorporated in pharmaceutical compositions.

24 Claims, No Drawings

DIPEPTIDES, THEIR PREPARATION AND COMPOSITIONS CONTAINING THEM

DESCRIPTION

The present invention relates to dipeptides which possess immunostimulant activity, to their preparation and to compositions containing them.

Bacterial walls, e.g. the walls of mycobacteria, essentially consist of a peptidoglycan, formed from N-acetylmuramic acid, to which peptides containing the sequence L-Ala-D-Glu-DAP are fixed: Ala represents alanine, Glu represents glutamine and DAP represents diaminopimelic acid. Furthermore, bacterial walls are very rich in lipids, some of which are free and can be extracted and others of which are bonded to the structure of the wall and comprise mycolic acids (α-branched and β-hydroxylic giant fatty acids). The constituents of the cell wall together form a covalent structure composed of a peptidoglycan and of an arabinogalactan mycolate, which are bonded to one another by means of phosphodiester linkages. These bacterial walls possess most of the biological properties of whole cells when they are associated with a mineral or vegetable oil and administered after being suspended in physiological solution.

Peptides, coupled with N-acetylmuramic acid, which contain the sequence L-Ala-D-Glu or L-Ser-D-Glu (in which Ser represents serine) and which are effective as immunological adjuvants and as anti-infectious agents are described in British Patent Specification Nos. 1,496,332 and 1,496,333 and in Belgian Patent Specification Nos. 852,348 and 852,349 (U.S. Pat. No. 4,153,684).

Products which result from the coupling of a fatty acid with a heptapeptide saccharide isolated from a mycobacterium containing a "D" wax, and which can be represented by the following formula:

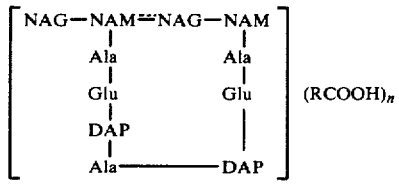

wherein, in particular, NAG represents N-acetylglycosamine, NAM represents N-acetylmuramic acid and R represents an alkyl radical containing 9 to 17 carbon atoms, are described in British Patent Specification No. 1,525,763. These products are immunological adjuvants for the production of antibodies and the potentiation of delayed hypersensitivity, which are capable of acting alone, i.e. it is not necessary to administer them in oily solution.

All these products are characterised by the presence of N-acetylmuramic acid, which, according to Kasumoto et al., Tetrahedron Letters, 49, 4,899 (1978), is considered to be associated with the immunological activity.

It has now been found that certain dipeptides possess remarkable adjuvant and immunostimulant properties, despite the absence of N-acetylmuramic acid. Furthermore, these compounds, which are well defined, can easily be obtained with the purity required for therapeutic use.

The present invention accordingly provides dipeptides of the formula:

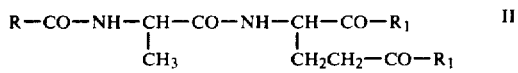

in which R-CO represents a fatty acid residue and the symbols $R_1$, which are identical or different, represent a hydroxyl or amino radical or an alkoxy radical of 1 to 4 carbon atoms, which is unsubstituted or substituted by a phenyl or nitrophenyl radical, it being understood that the residue of alanine [$NH_2$-$CH(CH_3)COOH$] is in the L form and that the residue of glutamic acid [$NH_2$-$CH(CH_2CH_2COOH)COOH$] or derivative thereof (amide or ester) is in the D form, and the metal salts and addition salts with nitrogen containing bases.

In the fatty acid residue R-CO, R may, for example, represent a hydrogen atom or an alkyl radical of 1 to 44 carbon atoms, which is unsubstituted or substituted by a hydroxyl, phenyl or cyclohexyl radical, an alkenyl radical of 2 to 29 carbon atoms containing one or more double bonds, or R-CO may represent a mycolic acid residue, such as that encountered in the structure of the bacterial wall of mycobacteria, Nocardia or Corynebacteria.

Especially valuable dipeptides are those in which R is alkyl of 1 to 23 carbon atoms or alkenyl of 2 to 23 carbon atoms containing one to four double bonds, the said alkyl or alkenyl being unsubstituted or substituted by hydroxyl, phenyl, or cyclohexyl, such that R contains at least seven but nor more than 29 carbon atoms, one of the radicals $R_1$ represents hydroxy or amino and the other represents hydroxy, amino, or benzyloxy.

According to a feature of the present invention, the dipeptides of the formula II can be obtained by methods generally used in peptide chemistry. The various reactions are carried out after the blocking, by means of suitable protective groups, of the amine or acid groups which must not participate in the reaction, and are followed, where appropriate, by the unblocking of these groups.

More particularly, the dipeptides of the formula (II) can be obtained by reacting an acid of the formula:

in which R is defined as above, or an activated derivative of this acid, with a dipeptide of the formula:

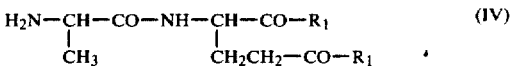

in which the symbols $R_1$, which are identical or different, are as defined above, this reaction optionally being followed by the replacement of the radical or radicals $R_1$ by a hydroxyl or amino radical, depending on the meanings of $R_1$.

In the formula (IV), if the radicals $R_1$, which are identical or different, represent an amino radical or an alkoxy radical containing 1 to 4 carbon atoms, which is optionally substituted by a phenyl or nitrophenyl radical, the acid of the formula (III) can be condensed with the dipeptide of the general formula (IV) in the presence of a condensation agent, such as dicyclohexylcarbodiimide, the reaction being carried out in an organic solvent, such as methylene chloride or dimethylformamide, at a temperature between −10° and +30° C.

In the formula (IV), if the radicals R₁ each represent a hydroxyl radical, or alternatively one of the radicals R₁ represents a hydroxyl radical and the other represents an amino or alkoxy radical defined as above, it is necessary to activate the acid of the general formula (III) before it is reacted with the dipeptide of the general formula (IV). An acid halide or a mixed anhydride, which is generally prepared in situ by reacting an alkyl halogenoformate (preferably isobutyl chloroformate) with the acid of the general formula (III) in the presence of a base, is particularly advantageously used as the activated acid.

If the acid of the general formula (III) is used in the form of a halide, more particularly the chloride, the reaction is carried out in an organic solvent, such as diethyl ether or methylene chloride, in the presence of a base (e.g. an inorganic base, such as sodium hydroxide, or an organic base, such as triethylamine), at a temperature between 0° and 30° C. In general, the dipeptide of the general formula (IV) is used in the form of a salt, such as the hydrochloride.

If the acid of the general formula (III) is used in the form of a mixed anhydride, the reaction is preferably carried out in an organic solvent, such as dioxane, tetrahydrofurane, chloroform, toluene or dimethylformamide, or in an aqueous-organic medium, in the presence of a base (e.g. an inorganic base, such as sodium hydroxide, or an organic base, such as triethylamine), at a temperature between −10° and +30° C. In general, the dipeptide of the general formula (IV) is used in the form of a salt, such as the hydrochloride.

The dipeptides of formula (II) in which the symbols R₁, which are identical or different, represent a hydroxyl or amino radical can be obtained from a dipeptide of the general formula (II) in which one of the symbols R₁ represents a hydroxyl, amino or alkoxy radical as defined above and the other represents a hydroxyl or alkoxy radical as defined above, by the usual methods which make it possible to convert either an ester group into a carboxyl or carbamoyl group or to convert a carboxyl group into a carbamoyl group.

In general, the conversion of an ester group into a carboxyl group can be carried out either by saponification under mild conditions or by hydrogenolysis, in particular if at least one of the symbols R₁ represents a benzyloxy or nitrobenzyloxy radical.

If hydrogenolysis is carried out with hydrogen, the reaction is generally carried out in a suitable organic solvent, such as acetic acid (if appropriate mixed with another organic solvent, such as methanol), or in an aqueous-organic medium, in the presence of a catalyst, such as palladium, e.g. palladium-on-charcoal, at a temperature of the order of 20° C. and under a pressure of the order of 760 mm Hg.

In general, the conversion of an ester or carboxyl group into a carbamoyl group is carried out with a solution of anhydrous ammonia in an organic solvent. If ammonia is reacted with a compound of the formula (II) in which at least one of the symbols R₁ represents an alkoxy radical as defined above, the reaction is advantageously carried out in methanol. If ammonia is reacted with a compound of the formula (II) in which at least one of the symbols R₁ represents a hydroxyl radical, it is necessary to activate the acid group or groups beforehand, generally in the form of a mixed anhydride prepared in situ by reaction with an alkyl halogenoformate, such as isobutyl chloroformate, and then to carry out the reaction under the conditions described above for the reaction of an activated derivative of an acid of the formula (III), in the form of a mixed anhydride, with the dipeptide of the formula (IV).

The dipeptide of the formula (IV) can be obtained by known methods by condensing L-alanine, in which the amine group is protected, with D-glutamic acid, in which the acid groups are protected if appropriate, and then removing the protective group from the amine group.

According to a further feature of the invention, the dipeptides of the formula (II) can be obtained by reacting a L-alanine derivative of the formula:

$$R—CO—NH—CH—COOH \quad \text{(V)}$$
$$\qquad\qquad\qquad\;\;|$$
$$\qquad\qquad\qquad\;\;CH_3$$

in which R is defined as above, with a D-glutamic acid derivative of the formula:

$$H_2N—CH—CO—R_1 \quad \text{(VI)}$$
$$\qquad\;\;|$$
$$\qquad\;\;CH_2CH_2—CO—R_1$$

in which the symbols R₁, which are identical or different, are as defined above, this reaction optionally being followed by the replacement of the radical or radicals R₁ by a hydroxyl or amino radical, depending on the meanings of R₁.

It is particularly advantageous to activate the acid group of the L-alanine derivative of the general formula (V), generally in the form of a mixed anhydride prepared in situ, before it is reacted with the compound of the general formula (VI), in particular if at least one of the symbols R₁ represents a hydroxyl radical. If the acid groups of the D-glutamic acid are protected, i.e. if the symbols R₁, which are identical or different, represent an amino or alkoxy radical as defined above, the acid of the formula (V) can be condensed with the D-glutamic acid derivative of the formula (VI) in the presence of a condensation agent, such as dicyclohexylcarbodiimide.

In general, the L-alanine derivative of the formula (V) is condensed with the D-glutamic acid derivative of the formula (VI) under the conditions described above for the condensation of the acid of the formula (III) with the aminoacid of the formula (IV).

The L-alanine derivative of the formula (V) can be obtained by reacting an acid of the formula (III) or an activated derivative of this acid with L-alanine, in which the acid group is protected, if appropriate, in the form of an ester, this reaction being followed, if necessary, by the removal of the protective group from the acid group.

If the acid group of the L-alanine is protected, the acid of the formula (V) is generally condensed in the presence of a condensation agent, such as dicyclohexylcarbodiimide, the reaction being carried out in an organic solvent, such as methylene chloride or dimethylformamide, at a temperature between −10° and +30° C.

If the acid group of the L-alanine is free, it is necessary to activate the acid of the formula (III) before it is reacted with the L-alanine. An acid halide or a mixed anhydride is particularly advantageously used as the activated derivative of the acid of the formula (III). The reaction is then carried out under the conditions described above for the reaction of an acid of the formula (III) with a dipeptide of the formula (IV).

According to yet a further feature of the invention, the dipeptides of the formula (II) in which the symbols $R_1$, which are identical or different, represent a hydroxyl or amino radical, at least one of them being a hydroxyl radical, and R is as defined above can be obtained by means of the Merrifield peptide synthesis in the solid phase. Thus, the dipeptides of the formula II can be obtained by carrying out the following stages in succession:

(1) fixing, to a suitable solid support, the α- or γ-carboxyl group of D-glutamic acid, in which the amine group is protected and in which the γ- or α-carboxyl group respectively is protected in the form of an amide or ester, (2) removing the protective group from the amine group without affecting the glutamic acid-support bond and, if appropriate, without affecting the ester group of the second carboxyl group of the D-glutamic acid, (3) condensing L-alanine, in which the amine group is protected by a suitable protective group, with the D-glutamic acid fixed to its support, (4) removing the protective group from the amine group of the L-alanine residue without affecting the D-glutamic acid-support bond and, if appropriate, without affecting the ester group of the second carboxyl group of the D-glutamic acid, (5) condensing the fatty acid RCOOH with the resulting dipeptide fixed to the support, (6) breaking the D-glutamic acid-support bond, if appropriate with removal of the protective group from the α- or γ-carboxyl group of the glutamic acid, and (7) separating the dipeptide of the formula (II) thus obtained.

Particularly suitable supports are chloromethylated or hydroxymethylated styrene/divinylbenzene copolymers. Preferably, chloromethylated styrene/divinylbenzene copolymers (98/2 or 99/1) are used.

The suitably protected D-glutamic acid is fixed to the chloromethylated support by the usual methods by reacting the aminoacid, dissolved in an organic solvent, such as ethanol, with the resin, in the presence of an organic base, such as triethylamine. It is particularly advantageous to heat the reaction mixture to a temperature close to the boiling point of the solvent.

The protective groups of the amine group and, if appropriate, of one of the acid groups of the D-glutamic acid must be chosen so that the protective group is removed from the amine group without affecting either the aminoacid-support bond or the protective group of the acid group.

In general, the acid group of the D-glutamic acid which must be protected is in the form of the benzyl ester, which is removed in an acid medium, e.g. by means of an anhydrous mixture of hydrogen bromide and trifluoroacetic acid, and the protective group of the amine group is the t-butoxycarbonyl radical, which is removed e.g. by a trifluoroacetic acid/methylene chloride mixture.

The L-alanine, in which the amine group is preferably protected by a t-butoxycarbonyl group, is condensed with the D-glutamic acid-support in accordance with the usual methods employed in peptide chemistry.

In general, the reaction is carried out in the presence of a condensation agent, such as dicyclohexylcarbodiimide, in an organic solvent, such as methylene chloride.

The protective group is removed from the amine group of the L-alanyl residue under the conditions indicated above for the removal of the protective group from the amine group of the D-glutamic acid.

The fatty acid is condensed with the resulting dipeptide-support in accordance with the usual methods and in particular in accordance with the method indicated above for the condensation of the L-alanine with the D-glutamic acid-support.

The breaking of the D-glutamic acid-support bond, which is of the benzyl ester type, and, if appropriate, the removal of the protective group from the carboxyl group of the D-glutamic acid, are generally carried out simultaneously. Preferably, an anhydrous mixture of hydrogen bromide and trifluoroacetic acid is used.

The product of the formula (II) is separated from the reaction mixture in accordance with the usual methods. The support is filtered off and the dipeptide of the formula (II) is separated from the filtrate after concentration to dryness and after purification in accordance with physicochemical methods.

In accordance with a variant of the process described above, it is possible to condense, with the D-glutamic acid-support, L-alanine in which the amine group is protected by a fatty acid residue as defined above. Under these conditions, the condensation of the L-alanine with the D-glutamic acid-support leads directly to the product of the formula (II), which is separated after breaking the D-glutamic acid-support bond and after removal, if appropriate, of the protective group from the acid group of the D-glutamic acid.

In accordance with another variant of the process described above, it is possible to fix, to the appropriate support, the dipeptide originating from the condensation of L-alanine with D-glutamic acid, then to condense the fatty acid with the dipeptide fixed in this way, and finally to separate the resulting product. During the fixing of the dipeptide to the support, it is necessary to protect the amine group of the L-alanyl residue and, if appropriate, the α-acid group of the D-glutamic acid, preferably by using the protective groups indicated above. Under these conditions, the condensation of the fatty acid with the dipeptide fixed to its support, from which the protective group of the amine group has been removed, leads directly to the product of the formula (II), which is separated after breaking the D-glutamic acid-support bond and, if appropriate, after removing the protective group from the acid group of the D-glutamic acid.

If necessary, the dipeptides of the general formula (II) can be purified by physical methods, such as crystallisation or chromatography.

The dipeptides according to the invention can be converted into metal salts or into addition salts with nitrogen-containing bases, depending on the nature of the substituent $R_1$.

The metal salts and the addition salts with organic bases can be obtained by reacting the new compounds with bases in an appropriate solvent. In general, the product is solubilised in water by adding the theoretical amount of base, and the resulting solution is then lyophilised.

The new compounds according to the present invention are useful as vaccine adjuvants and immunostimulants; they increase hypersensitivity reactions and/or the production of circulating antibodies against antigens with which they are administered, and they stimulate, in a non-specific manner, defence reactions against certain infections (e.g. the infection caused in mice by the intracellular bacterium *Listeria monocytogenes*).

In vitro, the compounds of general formula II are active at molar concentrations which are generally from $10^{-3}$ to $10^{-8}$, in particular in the following tests:

stimulating the synthesis of DNA (mitogenetic power), in accordance with the technique of G. Marchal, Ann. Immunol. (Inst. Pasteur), 125 C, 519 (1974), stimulating the allogenic reaction (histo-incompatibility reaction) in accordance with the technique of R. W. Dutton, J. exp. Med., 122, 759 (1966), and A. B. Peck and F. H. Bach, J. Immunol. Methods, 3, 147 (1973).

stimulating the production of antibodies, in accordance with the technique of P. H. Klesius, Proc. Soc. exp. Biol. Med. (N.Y.), 135, 155 (1970), and H. van Dijk and N. Bloksma, J. Immunol. Methods, 14, 325 (1977), increasing the number of phagocytic macrophages, in accordance with the technique of J. Michl et al., J. exp. Med., 144, 1,465 (1976), and stimulating the acid phosphatase and N-acetylglucosamidinase activity (lysosome enzymes of macrophages) in the absence of an increase in the lactate dehydrogenase, in accordance with the technique of P. Davies et al., J. exp. Med., 139, 1,262 (1974).

In vivo, in mice, at doses of between 1 and 30 mg/kg, they increase the delayed hypersensitivity and the production of antibodies, in particular in accordance with the technique of T. E. Miller et al., J. Nath. Cancer Inst., 51, 1,669 (1973).

In guinea-pigs, they increase the hypersensitivity reaction and the production of antibodies against bovine gamma-globulin coupled with the hapten dinitrophenol, in accordance with the technique of F. Floc'h et al., Immunol. Communic., 7, 41 (1978).

In mice, they stimulate the defence reactions against the infection caused in mice by Listeria monocytogenes, at doses of between 1 and 100 mg/kg, in accordance with the technique of R. M. Fauve and B. Hevin, C.R. Acad. Sci. (D), 285, 1,589 (1977).

In mice, they stimulate the ability of the reticuloendothelial system to take up colloidal carbon, in accordance with the technique of B. N. Halpern et al., Ann. Institut Pasteur, 80,582 (1951).

In rabbits, at doses which are generally between 0.1 and 3 mg/kg, they stimulate the formation of serum antibodies against influenza virus, in accordance with the technique of G. H. Werner et al., Biomedicine, 22, 440 (1975).

Of very particular value are the compounds of the formula (II) in which the symbols $R_1$, which are identical or different, represent a hydroxyl or amino radical or a benzyloxy radical and R-CO represents an alkanoyl or alkenoyl radical containing 8 to 20 carbon atoms.

The following Examples illustrate the invention.

The dipeptides of formula (II) can form complexes with alkali metals or alkaline earth metals. Consequently, the results of elementary analysis can deviate substantially from the theoretical values. However, the products are identified by their aminoacid content, by the C/N ratio and by their homogeneity in thin layer chromatography on silica gel.

EXAMPLE I

Lauroyl chloride (8 g) dissolved in diethyl ether (75 cc) is added, in the course of 37 minutes, to a solution of benzyl L-alanyl-α-D-glutamate hydrochloride (12.75 g) in 1 N sodium hydroxide solution (75 cc), and 1 N sodium hydroxide solution (37.4 cc) is added simultaneously to keep the pH of the reaction mixture between 8 and 9. The mixture is stirred for 1 hour 20 minutes. After decantation, the aqueous phase is acidifed to pH 2 by adding 1 N hydrochloric acid (60 cc) and extracted 3 times with ethyl acetate (300 cc in total). The combined organic extracts are washed with water (25 cc), dried over anhydrous sodium sulphate and concentrated to dryness under reduced pressure (20 mm Hg) at 45° C. to yield a white solid (7.4 g) which is chromatographed on neutral silica gel (80 g) contained in a column of diameter 2 cm. Elution is carried out successively with a mixture of ethyl acetate and methanol (8/2 by volume; 100 cc) and a mixture of ethyl acetate and methanol (1/1 by volume; 200 cc), 50 cc fractions being collected. Fraction 1 is concentrated to dryness under reduced pressure (20 mm Hg) at 45° C. to yield benzyl N-lauroyl-L-alanyl-α-D-glutamate (2 g) which melts at 130° C. Fractions 2 to 4 are likewise concentrated to dryness and chromatographed on neutral silica gel (0.063–0.20 mm; 100 g) contained in a column of diameter 2 cm. Elution is carried out with acetone (250 cc), 25 cc fractions being collected. Fractions 1 and 2 are concentrated to dryness under reduced pressure (20 mm Hg) at 45° C. to yield benzyl N-lauroyl-L-alanyl-α-D-glutamate (4.07 g) which melts at 130° C. and has the following characteristics:

Rf=0.9 [silica gel; n-butanol/pyridine/acetic acid/water (50/20/6/24 by volume)]

analysis: calculated C 66.10%, H 8.63%, N. 5.71%: found: 66.3%, 8.8%, 5.6%.

Benzyl L-alanyl-α-D-glutamate hydrochloride can be prepared in the following manner:

Benzyl N-t-butoxycarbonyl-L-alanyl-α-D-glutamate (97.16 g) is dissolved in a 1.7 N anhydrous solution of hydrogen chloride in acetic acid (970 cc). The resulting solution is stirred for 2 hours, anhydrous diethyl ether (3.8 liters) is then added rapidly and the mixture is left to stand for 2 hours at 0° C. The oily precipitate which has formed is separated from the supernatant liquor by decantation and dissolved in acetone (500 cc); the solution thus obtained is concentrated to dryness under reduced pressure (20 mm Hg) at 50° C. to yield benzyl-L-alanyl-α-D-glutamate hydrochloride (88.9 g).

Benzyl N-t-butoxycarbonyl-L-alanyl-α-D-glutamate can be prepared in accordance with the method of E. Bricas et al., Biochemistry 9, 823 (1970).

EXAMPLE 2

Isobutyl chloroformate (31 cc) is added to a solution, kept at a temperature of the order of 10° C., of lauric acid (47.75 g) in dioxan (3 liters) and triethylamine (33.3 cc). The mixture is stirred for 20 minutes at 10° C. and a solution, cooled to 10° C., of benzyl L-alanyl-α-D-glutamate hydrochloride (88.95 g) in a mixture of dioxan (1 liter), water (476 cc) and 1 N sodium hydroxide solution (476 cc) is then added in the course of 10 minutes. The reaction mixture is stirred for 1 hour at 10° C. and then for 18 hours at a temperature of the order of 20° C.; it is then diluted by adding water (4 liters), acidified to pH 2 by adding 1 N hydrochloric acid (about 475 cc) and kept for 2 hours at 0° C. The resulting precipitate is filtered off, washed successively with water (500 cc) and diethyl ether (500 cc) and then dried under reduced pressure (20 mm Hg) at 20° C. The product is suspended in ether (800 cc), the suspension is stirred for 1 hour and the product is filtered off and washed twice with ether (200 cc in total). After drying under reduced pressure (20 mm Hg) at 20° C., benzyl N-lauroyl-L-alanyl-α-D-glutamate (71.79 g), which melts at 130° C., is obtained.

Rf=0.77 [silica gel; ethyl acetate/methanol (4/1 by volume)]

EXAMPLE 3

Lauroyl chloride (5.49 g) dissolved in methylene chloride (150 cc) is added dropwise, in the course of 30 minutes, to a mixture, cooled to about 5° C., of benzyl L-alanyl-D-glutaminate hydrochloride (8.46 g) in methylene chloride (300 cc) and triethylamine (4.3 cc). The reaction mixture is stirred for 2¼ hours at about 20° C. and then extracted 3 times with water (1,500 cc in total). The organic phase is concentrated to about 100 cc under reduced pressure (20 mm Hg) at 40° C. The precipitate formed in the concentrate is filtered off and dried. This yields a white powder (5.3 g) with which a product (0.8 g) prepared under the same conditions is combined. The mixture is dissolved in boiling methanol (100 cc) and the resulting solution is left to stand for 3 hours at 0° C. The crystals formed are filtered off and dried under reduced pressure (0.2 mm Hg) at 50° C. This yields benzyl N-lauroyl-L-alanyl-D-glutaminate (4.64 g) which melts at 182° C.

Rf=0.80 [silica gel; ethyl acetate/methanol (1/1 by volume)]

Analysis: calculated %=C 66.23, H 8.85, N 8.58: found=66.1, 8.8, 8.4.

Benzyl L-alanyl-D-glutaminate hydrochloride can be prepared in the following manner:

Benzyl N-t-butoxycarbonyl-L-alanyl-D-glutaminate (5.2 g) is dissolved in a 1.7 N anhydrous solution of hydrogen chloride in acetic acid (60 cc). The resulting solution is stirred for 1 hour and the reaction mixture is poured into diethyl ether (300 cc). The ether phase is decanted. Diethyl ether (1 liter) is added to the residual gum, the gum is triturated, the ether phase is again decanted and the residue is taken up in methanol (200 cc). The resulting solution is concentrated to dryness under reduced pressure (20 mm Hg and then 0.2 mm Hg) at 50° C. This yields benzyl L-alanyl-D-glutaminate hydrochloride (4.3 g) in the form of a hard foam.

Benzyl N-t-butoxycarbonyl-L-alanyl-D-glutaminate can be prepared in accordance with the method of S. KUSUMOTO et al., Bull. Chem. Soc. Japan, 49, 533 (1976).

EXAMPLE 4

Benzyl N-lauroyl-L-alanyl-D-glutaminate (3.7 g) is dissolved in a mixture of methanol (1 liter), acetic acid (400 cc) and water (40 cc). Palladium-on-charcoal (containing 3% of palladium) (3.7 g) is added and a slow stream of hydrogen is passed through the mixture for 2 hours. The reaction mixture is filtered and the filtrate is diluted by adding water (3 liters). The insoluble material is filtered off and dried under reduced pressure (20 mm Hg) at 50° C. This yields N-lauroyl-L-alanyl-D-glutamine (2.3 g) which melts at 170°-172° C.

Rf=0.83 [silica gel; methanol]

Analysis: calculated %=C 60.12, H 9.33, N 10.52: found=60.1, 8.8, 10.5.

EXAMPLE 5

Benzyl N-lauroyl-L-alanyl-α-D-glutamate (500 mg) is dissolved in a mixture of methanol, acetic acid and water (25/1/1 by volume) (25 cc). Palladium-on-charcoal (containing 3% of palladium) (500 mg) is added and a slow stream of hydrogen is passed through the mixture for 2 hours. The reaction mixture is filtered and the filtrate is concentrated to dryness under reduced pressure (20 mm Hg) at 45° C. This yields a creamy white solid (460 mg) to which a product (690 mg) prepared under the same conditions is added. The mixture is dissolved in boiling methanol (10 cc), and water (5 cc) is added to the solution thus obtained. After standing for 20 hours at about 20° C., the white crystals which have appeared are filtered off, washed with a mixture of methanol and water (2/1 by volume) (5 cc) and then dried under reduced pressure (0.2 mm Hg) at 50° C. This yields N-lauroyl-L-alanyl-D-glutamic acid (770 mg) which melts at 138°-142° C.

Rf=0.61 [silica gel; n-butanol/pyridine/acetic acid/water (50/20/6/24 by volume)]

Analysis: calculated %=C 59.98, H 9.06, N 6.99, O 23.97: found=59.7, 9.0, 7.3, 24.1.

EXAMPLE 6

Isobutyl chloroformate (2.54 cc) is added to a solution, kept at 0° C., of lauric acid (3.9 g) in anhydrous toluene (156 cc) and triethylamine (2.7 cc). The mixture is stirred for 20 minutes at 0° C. and a solution, cooled to 0° C., of benzyl L-alanyl-D-isoglutaminate hydrochloride (6.7 g) in water (52 cc) and triethylamine (2.7 cc) is then added. The reaction mixture is stirred for 65 hours at a temperature of the order of 20° C. to yield a reaction mixture of gelatinous appearance, to which ethyl acetate (150 cc) is added. The precipitate is filtered off, washed with water (30 cc) and then dried to yield benzyl N-lauroyl-L-alanyl-D-isoglutaminate (7.6 g) in the form of a white powder. The aqueous phase of the above filtrate is extracted twice with ethyl acetate (100 cc in total), the ethyl acetate phase is combined with the organic phase of the filtrate and the combined phase is washed with 0.1 N hydrochloric acid (125 cc) and water (120 cc), dried over magnesium sulphate and then concentrated to dryness under reduced pressure (20 mm Hg) at 50° C. to yield a further 1.5 g of benzyl N-lauroyl-L-alanyl-D-isoglutaminate. The product (7.6 g and 1.5 g) is recrystallized from methanol (120 cc) to yield benzyl N-lauroyl-L-alanyl-D-isoglutaminate (6.6 g) which melts at 169° C.

Rf=0.13 [silica gel; ethyl acetate]

Benzyl L-alanyl-D-isoglutaminate hydrochloride can be prepared in accordance with the method of S. Kusumoto, Bull. Chem. Soc. Japan 49, 533 (1976).

EXAMPLE 7

Benzyl N-lauroyl-L-alanyl-D-isoglutaminate (6.6 g) is dissolved in acetic acid (330 cc). Palladium on charcoal (containing 3% w/w of palladium; 6.6 g) is added and a slow stream of hydrogen is then passed through the mixture for 2 hours. After filtering the reaction mixture, the filtrate is poured into water (3 liters). After standing for 2 hours at 0° C., the precipitate which has appeared is filtered off, washed twice with water (80 cc in total) and then dried to yield a product (5.16 g) to which a product (0.5 g) obtained under similar conditions is added. This mixture is dissolved in boiling methanol (90 cc), and water (45 cc) is added to the resulting solution. After standing for 2 hours at a temperature of the order of 20° C., the crystals which have appeared are filtered off, washed twice with water (60 cc in total) and dried under reduced pressure (20 mm Hg). This yields N-lauroyl-L-alanyl-D-isoglutamine (5.1 g) which melts at 163° C.

Rf=0.18 [silica gel; ethyl acetate/methanol (4/1 by volume)]

Analysis: calculated %=C 60.12, H 9.33, N 10.52: found=60.2, 9.5, 10.9.

EXAMPLE 8

Isobutyl chloroformate (0.53 cc) is added to a solution, kept at −10° C., of benzyl N-lauroyl-L-alanyl-α-D-glutamate (2 g) in chloroform (20 cc) and triethylamine (0.57 cc). The solution is stirred for 15 minutes at between −10° and −2° C. and a stream of ammonia is then passed through the reaction mixture for about 6 hours. The mixture is then left to stand for 68 hours at about 20° C. The reaction mixture is concentrated to dryness under reduced pressure (20 mm Hg) at 50° C. The residue is taken up in boiling isopropanol (50 cc). A very small amount of insoluble material is filtered off. After cooling the filtrate for 2 hours at 0° C., the precipitate which has appeared is filtered off and then dried. This yields N-lauroyl-L-alanyl-D-glutamamide (0.69 g) which melts at 226°-228° C.

Rf=0.75 [silica gel; ethyl acetate/methanol (1/1 by volume)]

Analysis: calculated %=C 60.27, H 9.61, N 14.06: found=59.3, 9.6, 14.1.

EXAMPLE 9

Isobutyl chloroformate (0.79 cc) is added to a solution, kept at about −5° C., of 5-phenylvaleric acid (1.09 g) in a mixture of tetrahydrofuran (50 cc) and triethylamine (0.86 cc). The mixture is stirred for 35 minutes at a temperature of the order of −5° C. and a solution, cooled to 0° C., of benzyl L-alanyl-α-D-glutamate hydrochloride (2.1 g) in tetrahydrofuran (50 cc), water (10 cc) and triethylamine (1.72 cc) is then added. The reaction mixture is stirred for 20 hours at about 20° C. and then concentrated to dryness under reduced pressure (20 mm Hg) at 40° C. The resulting residue is dissolved in water (100 cc) and the resulting solution is acidified to pH 2 by adding a 1 N solution of hydrochloric acid. The precipitate which has appeared is filtered off and washed twice with water (50 cc in total) and twice with diethyl ether (50 cc in total). After drying, benzyl N-(5-phenylvaleryl)-L-alanyl-α-D-glutamate (1.98 g), which melts at 128° C., is thus obtained.

Rf=0.72 [silica gel; n-butanol/pyridine/acetic acid/water (50/20/6/24 by volume)]

EXAMPLE 10

Benzyl N-(5-phenylvaleryl)-L-alanyl-α-D-glutamate (1.8 g) is dissolved in acetic acid (100 cc). Palladium-on-charcoal (containing 3% of palladium) (1.8 g) is added and a stream of hydrogen is passed through the mixture for 4 hours. The reaction mixture is filtered. The filtrate is concentrated to dryness under reduced pressure (20 mm Hg) at 60° C. The residue is taken up in boiling ethyl acetate (100 cc); the insoluble material is removed by filtration. The resulting filtrate is diluted by adding isopropyl ether (400 cc). After standing for 2 hours at 0° C., the crystals which have appeared are filtered off and dried. This yields N-(5-phenylvaleryl)-L-alanyl-D-glutamic acid (0.66 g) which melts at between 135° C. and 140° C. (giving a paste).

Rf=0.55 [silica gel; n-butanol/pyridine/acetic acid/water (50/20/6/24 by volume)]

Analysis: calculated %=C 60.31, H 6.93, N 7.40: found=60.3, 7.1, 7.4.

EXAMPLE 11

Isobutyl chloroformate (3.6 cc) is added to a solution, kept at −1° C., of octanoic acid (3.95 g) in tetrahydrofuran (140 cc) and triethylamine (3.8 cc). The mixture is stirred for 20 minutes at −1° C. and a solution, cooled to 0° C., of benzyl L-alanyl-α-D-glutamate hydrochloride (9.45 g) in a mixture of 1 N sodium hydroxide solution (54.8 cc) and water (30 cc) is then added. The reaction mixture is stirred for 1 hour at −1° C. and then for 20 hours at about 20° C. It is then acidified to pH 1 by adding 1 N hydrochloric acid. The tetrahydrofuran is evaporated off under reduced pressure (20 mm Hg) at 45° C. and the concentrate is then extracted with ethyl acetate (100 cc). The organic phase thus obtained is washed twice with 1 N hydrochloric acid (50 cc in total) and with a saturated solution of sodium chloride (25 cc) and concentrated to dryness under reduced pressure (20 mm Hg) at 45° C. to yield a pale yellow oil (10 g) which is chromatographed on a column of diameter 2.5 cm, containing neutral silica gel (0.063–0.20 mm; 200 g). Elution is carried out with ethyl acetate, 100 cc fractions being collected. Fractions 7 to 9 are combined and concentrated to dryness under reduced pressure (20 mm Hg) at 45° C. The resulting residue is triturated in a mixture of diethyl ether and petroleum ether (b.p.=35°-60° C.) (¼ by volume; 100 cc), filtered off and dried. Benzyl N-octanoyl-L-alanyl-α-D-glutamate (3.27 g) is thus obtained in the form of a white powder.

Rf=0.56 [silica gel; ethyl acetate/methanol (8/2 by volume)]

EXAMPLE 12

Isobutyl chloroformate (3.6 cc) is added to a solution, kept at 0° C., of palmitic acid (7.03 g) in tetrahydrofuran (140 cc) and triethylamine (3.8 cc). The mixture is stirred for 20 minutes at 0° C. and a solution, cooled to 0° C., of benzyl L-alanyl-α-D-glutamate hydrochloride (9.45 g) in a mixture of 1 N sodium hydroxide solution (54.8 cc) and water (30 cc) is then added. The reaction mixture is stirred for 1 hour at 0° C. and then for 18 hours at about 20° C.; it is then acidified to pH 1 by adding 1 N hydrochloric acid (70 cc). The precipitate formed is filtered off, washed 5 times with water (200 cc in total) and dried to yield a white powder (12.11 g) which is chromatographed on a column of diameter 2.5 cm, containing neutral silica gel (0.063–0.20 mm; 200 g). Elution is carried out successively with ethyl acetate (200 cc), a mixture of ethyl acetate and methanol (9/1 by volume; 300 cc), a mixture of ethyl acetate and methanol (8/2 by volume; 1.6 liters) and a mixture of ethyl acetate and methanol (6/4 by volume; 400 cc), 100 cc fractions being collected. Fractions 5 to 23 are combined and concentrated to dryness under reduced pressure (20 mm Hg) at 45° C. to yield a solid (5.18 g) which is triturated in boiling diethyl ether (50 cc) for ¼ hour. After cooling to a temperature of the order of 20° C., the insoluble material is filtered off, washed 3 times with diethyl ether (75 cc in total) and then dried. Benzyl N-palmitoyl-L-alanyl-α-D-glutamate (2.94 g) is thus obtained.

Rf=0.77 [silica gel; ethyl acetate]

EXAMPLE 13

Isobutyl chloroformate (0.48 cc) is added to a solution, kept at 31 5° C., of arachidonic acid (1.12 g) in tetrahydrofuran (40 cc) and triethylamine (0.52 cc). The mixture is stirred for 35 minutes at between −5° C. and −8° C. and a solution, cooled to 0° C., of L-alanyl-D-glutamic acid hydrochloride (0.93 g) in a mixture of tetrahydrofuran (20 cc), water (15 cc) and triethylamine (1.55 cc) is then added. The reaction mixture is stirred for 1 hour at a temperature of the order of −3° C. and then for 20 hours at a temperature of the order of 20° C.; it is then diluted by adding water (50 cc), acidified to pH 2 by adding a 1 N aqueous solution of hydrochloric acid and extracted 3 times with diethyl ether (75 cc in total). The combined ether phases are concentrated to dryness under reduced pressure (20 mm Hg) at 30° C. This yields a yellow oil (2.5 g) which is chromatographed on a column of diameter 2.4 cm, containing neutral silica gel (0.04–0.063 mm) (50 g). Elution is carried out with ethyl acetate. This yields N-arachidonoyl-L-alanyl-D-glutamic acid (0.32 g) which melts at about 90° C. (giving a paste).

Rf=0.70 [silica gel; n-butanol/pyridine/acetic acid/water (50/20/6/24 by volume)]

L-Alanyl-D-glutamic acid hydrochloride can be prepared in accordance with the method of H. NGUYEN-HUY et al., Eur. J. Biochem., 66, 79 (1976).

EXAMPLE 14

Isobutyl chloroformate (0.48 cc) is added to a solution, kept at −10° C., of palmitic acid (0.94 g) in tetrahydrofuran (40 cc) and triethylamine (0.52 cc). The mixture is stirred for 50 minutes at between −6° C. and −8° C. and a solution, cooled to 0° C., of L-alanyl-D-glutamic acid hydrochloride (0.93 g) in a mixture of tetrahydrofuran (20 cc), water (15 cc) and triethylamine (1.55 cc) is then added. The reaction mixture is stirred for 1 hour at a temperature of the order of −6° C. and then for 20 hours at a temperature of the order of 20° C.; it is then acidified to pH 2 by adding a 4 N aqueous solution of hydrochloric acid and diluted by adding water (300 cc). The precipitate formed is filtered off, washed 3 times with diethyl ether (150 cc in total) and dried. This yields a white powder (1.08 g) which is dissolved in boiling ethyl acetate (120 cc), the solution being filtered hot. After standing for 20 hours at about 4° C., the precipitate formed is filtered off, washed twice with ethyl acetate (20 cc in total) and dried in air. This yields a white powder (0.93 g) which is dissolved in boiling acetic acid (15 cc), the solution being filtered hot. After standing for 64 hours at about 4° C., the precipitate formed is filtered off, washed twice with ethyl acetate (20 cc in total) and dried under reduced pressure (0.2 mm Hg) at 50° C. This yields N-palmitoyl-L-alanyl-D-glutamic acid (0.5 g) which melts at 155° C.

Rf=0.62 [silica gel; n-butanol/pyridine/acetic acid/water (50/20/6/24 by volume)]

Analysis: calculated %=C 63.13, H 9.71, N 6.14: found=63.0, 9.3, 6.2.

EXAMPLE 15

Isobutyl chloroformate (1.95 cc) is added to a solution, kept at 25° C., of docosanoic acid (5.19 g) in a mixture of tetrahydrofuran (150 cc) and triethylamine (2.1 cc). The mixture is stirred for 20 minutes at 25° C. and a solution of benzyl L-alanyl-α-D-glutamate hydrochloride (5.69 g) in a mixture of 1 N sodium hydroxide solution (33 cc) and water (17 cc) is then added. The reaction mixture is stirred for 30 minutes at about 30° C. and then for 18 hours at about 20° C. Water (100 cc) is then added and the mixture is acidified to pH 1 by adding 1 N hydrochloric acid (35 cc). This yields a precipitate which is filtered off, washed 3 times with water (75 cc in total) and dried under reduced pressure (0.3 mm Hg) at 20° C. This yields a white powder (6.53 g). This powder (6 g) is dissolved in tetrahydrofuran (50 cc) containing neutral silica gel (0.04–0.063 mm) (20 g). The mixture is concentrated to dryness under reduced pressure (20 mm Hg) at 50° C. and the whole is introduced onto a column of diameter 3.5 cm, containing neutral silica gel (0.04–0.063 mm) (180 g). Elution is carried out successively with a mixture of cyclohexane and ethyl acetate (1/1 by volume) (1,300 cc), ethyl acetate (600 cc), a mixture of ethyl acetate and tetrahydrofuran (95/5 by volume) (500 cc), a mixture of ethyl acetate and tetrahydrofuran (9/1 by volume) (900 cc), a mixture of ethyl acetate and tetrahydrofuran (8/2 by volume) (800 cc), a mixture of ethyl acetate and tetrahydrofuran (6/4 by volume) (1,000 cc), a mixture of ethyl acetate and tetrahydrofuran (4/6 by volume) (900 cc), a mixture of ethyl acetate and tetrahydrofuran (2/8 by volume) (500 cc) and tetrahydrofuran (600 cc), 100 cc fractions being collected. Fractions 17 to 68 are combined and concentrated to dryness under reduced pressure (20 mm Hg) at 50° C. This yields benzyl N-docosanoyl-L-alanyl-α-D-glutamate (3.31 g).

Rf=0.54 [silica gel; ethyl acetate/tetrahydrofuran (8/2 by volume)]

EXAMPLE 16

Isobutyl chloroformate (3 cc) is added to a solution, kept at −5° C., of 3-cyclohexanepropionic acid (3.605 g) in a mixture of tetrahydrofuran (100 cc) and triethylamine (3.23 cc). The mixture is stirred for 20 minutes at −5° C. and a solution, cooled to 5° C., of benzyl L-alanyl-α-D-glutamate hydrochloride (7.96 g) in a mixture of 1 N sodium hydroxide solution (46.2 cc) and water (13.8 cc) is then added. The reaction mixture is stirred for 10 minutes at 0° C. and then for 2 days at about 20° C. The tetrahydrofuran is then evaporated off under reduced pressure (20 mm Hg) at 50° C. The concentrate is extracted twice with diethyl ether (80 cc in total) and acidified to pH 1 by adding 1 N hydrochloric acid (50 cc). The oil which separates out from the reaction medium is extracted 4 times with ethyl acetate (200 cc in total). The combined organic phases are washed with a saturated solution of sodium chloride (25 cc) and dried over anhydrous magnesium sulphate. Concentration to dryness under reduced pressure (20 mm Hg) at 50° C. yields an oil which crystallises spontaneously. These crystals (7.3 g) are dissolved in acetic acid (40 cc) containing neutral silica gel (0.04–0.063 mm) (20 g). The mixture is concentrated to dryness and the whole is introduced onto a column of diameter 2.5 cm, containing neutral silica gel (0.04–0.063 mm) (50 g). Elution is carried out with ethyl acetate, 100 cc fractions being collected. The 4th fraction is concentrated to dryness under reduced pressure (20 mm Hg) at 45° C. This yields benzyl N-(3-cyclohexylpropionyl)-L-alanyl-α-D-glutamate (1.86 g) which melts at 126°-128° C. Fractions 3 and 5 are combined and concentrated to dryness. The amorphous solid is chromatographed on a column of diameter 2.5 cm, containing neutral silica gel (0.04–0.063 mm) (68 g). Elution is carried out successively with a mixture of cyclohexane and ethyl acetate (1/1 by volume) (520 cc) and ethyl acetate (520 cc), 40 cc fractions being collected. Fractions 11 to 28 are combined and concentrated to dryness under reduced pressure (20 mm Hg) at 45° C. This yields benzyl N-(3- cyclohexylpropionyl)-L-alanyl-α-D-glutamate (1.37 g) which melts at 128°-130° C.

Rf=0.14 [silica gel; ethyl acetate]

EXAMPLE 17

Isobutyl chloroformate (4.3 cc) is added to a solution, kept at −6° C., of N-(3,5,5-trimethylhexanoyl)-L-alanine (7.59 g) in a mixture of tetrahydrofuran (400 cc) and triethylamine (4.63 cc). The mixture is stirred for 20 minutes at −6° C. and a solution, cooled to 3° C., of benzyl α-D-glutamate hydrochloride (9.06 g) in a mixture of 1 N sodium hydroxide solution (66.2 cc) and water (14 cc) is then added. The reaction mixture is stirred for 15 minutes at about −5° C. and then for 66 hours at about 18° C.; it is then acidified to pH 1 by adding 1 N hydrochloric acid (75 cc). The tetrahydrofuran is evaporated off under reduced pressure (20 mm Hg) at 50° C. The concentrate is extracted 5 times with ethyl acetate (200 cc in total). The combined ethyl acetate phases are washed with 0.1 N hydrochloric acid (40 cc) and dried over magnesium sulphate. Filtration and concentration to dryness under reduced pressure (20 mm Hg) at 50° C. yields an oil (14.8 g) which is dissolved in ethyl acetate (50 cc) containing neutral silica gel (0.04–0.063 mm; 30 g). The mixture is concentrated to dryness under reduced pressure (20 mm Hg) at 50° C. and then introduced onto a column of diameter 2.8 cm, containing neutral silica gel (0.04–0.063 mm; 280 g). Elution is carried out successively with cyclohexane (2 liters), a mixture of cyclohexane and ethyl acetate (95/5 by volume; 1 liter), a mixture of cyclohexane and ethyl acetate (90/10 by volume; 1.5 liters), a mixture of cyclohexane and ethyl acetate 80/20 by volume; 5 liters), a mixture of cyclohexane and ethyl acetate (70/30 by volume; 1.5 liters) and a mixture of cyclohexane and ethyl acetate (50/50 by volume; 3.5 liters), 500 cc fractions being collected. Fractions 23 to 29 are combined and concentrated to dryness under reduced pressure (20 mm Hg) at 50° C. Benzyl N-(3,5,5-trimethylhexanoyl)-L-alanyl-α-D-glutamate (10.86 g) is thus obtained in the form of an oil which crystallises.

Rf=0.37 [silica gel; ethyl acetate]

N-(3,5,5-Trimethylhexanoyl)-L-alanine can be prepared in the following manner:

Isobutyl chloroformate (6.5 cc) is added to a solution, kept at −5° C., of 3,5,5-trimethylhexanoic acid (7.912 g) in a mixture of tetrahydrofuran (125 cc) and triethylamine (7 cc). The mixture is stirred for 20 minutes at −5° C. and a solution, cooled to 5° C., of L-alanine (4.495 g) in 1 N sodium hydroxide solution (50 cc) is then added. The reaction mixture is stirred for 10 minutes at about 0° C. and then for 18 hours at about 25° C. The tetrahydrofuran is then evaporated off under reduced pressure (20 mm Hg) at 50° C. The concentrate is extracted twice with diethyl ether (40 cc in total) and acidified to pH 1 by adding 1 N hydrochloric acid (55 cc). The oily precipitate which forms is extracted 5 times with ethyl acetate (250 cc in total). The ethyl acetate phases are combined, washed with a saturated solution of sodium chloride (25 cc) and dried over magnesium sulphate. Filtration and concentration to dryness under reduced pressure (20 mm Hg) at 50° C. yields an oil (11.79 g) which is dissolved in ethyl acetate (40 cc) containing neutral silica gel (0.063–0.20 mm; 20 g). The mixture is concentrated to dryness under reduced pressure (20 mm Hg) at 50° C. and then introduced onto a column of diameter 3 cm, containing neutral silica gel (0.063–0.20 mm; 120 g). Elution is carried out successively with cyclohexane (600 cc), a mixture of cyclohexane and ethyl acetate (95/5 by volume; 300 cc), a mixture of cyclohexane and ethyl acetate (90/10 by volume; 300 cc) a mixture of cyclohexane and ethyl acetate (80/20 by volume; 300 cc), a mixture of cyclohexane and ethyl acetate (50/50 by volume; 700 cc), ethyl acetate (300 cc) and a mixture of ethyl acetate and methanol (90/10 by volume; 300 cc), 100 cc fractions being collected. Fractions 17 to 28 are combined and concentrated to dryness under reduced pressure (20 mm Hg) at 45° C. This yields an oil (10.16 g) which is dissolved in diethyl ether (25 cc). The addition of petroleum ether (150 cc) yields an oil which is separated off by decantation. After drying in vacuo (0.2 mm Hg), N-(3,5,5-trimethylhexanoyl)-L-alanine (7.59 g) is obtained.

Rf=0.43 [silica gel; ethyl acetate]

EXAMPLE 18

Succinimide 2-n-pentyl-3-hydroxynonanoate (27.5 g) dissolved in 1,2-dimethoxyethane (644 cc) is added, in the course of 1 hour 10 minutes, to a solution, kept at 7° C., of benzyl L-alanyl-α-D-glutamate hydrochloride (27.8 g) in a mixture of water (245 cc) and triethylamine (22.9 cc). The reaction mixture is kept at 20° C. for 20 hours and then at 60° C. for 5 hours. The 1,2-dimethoxyethane is then evaporated off under reduced pressure (20 mm Hg) at 50° C.; the concentrate is acidified to pH 1 by adding 1 N hydrochloric acid (150 cc) and extracted 5 times with ethyl acetate (1.5 liters in total). The combined ethyl acetate phases are washed 3 times with water (750 cc in total), dried over sodium sulphate and concentrated to dryness under reduced pressure (20 mm Hg) at 60° C. to yield an oil (38.6 g) which is dissolved in ethyl acetate (200 cc). Dicyclohexylamine (13 g) is added thereto. After standing for 20 hours at 4° C., the white solid formed is filtered off, washed twice with ethyl acetate (40 cc in total) and twice with diethyl ether (200 cc in total) and dried under reduced pressure (20 mm Hg) at 20° C. to yield a white powder (22.4 g) to which a product (1.9 g) obtained in a similar operation is added. The mixture is dissolved in water (500 cc); ethyl acetate (200 cc) and a saturated solution of citric acid (150 cc) are added to the aqueous solution. The organic phase is extracted twice with ethyl acetate (400 cc in total). The combined ethyl acetate phases are washed twice with water (200 cc in total), dried over sodium sulphate and concentrated to dryness under reduced pressure (20 mm Hg) at 60° C. Benzyl N-(2-n-pentyl-3-hydroxynonanoyl)-L-alanyl-α-D-glutamate (17.4 g) is thus obtained in the form of a beige paste.

Rf=0.25 [silica gel; ethyl acetate]

Succinimide 2-n-pentyl-3-hydroxynonanoate can be prepared in the following manner:

Dicyclohexylcarbodiimide (27 g) dissolved in 1,2-dimethoxyethane (300 cc) is added, in the course of 40 minutes, to a solution, kept at 0° C., of 2-n-pentyl-3-hydroxynonanoic acid (29.1 g) and N-hydroxysuccinimide (14.1 g) in 1,2-dimethoxyethane (300 cc). The reaction mixture is stirred at 0° C. for 3 hours and then kept at 4° C. for 21 hours. The precipitate formed is filtered off and washed twice with 1,2-dimethoxyethane (100 cc in total). The filtrate is concentrated to dryness under reduced pressure (20 mm Hg) at 50° C. The concentrate is taken up in a mixture of diisopropyl ether (300 cc) and acetic acid (3 cc). After standing for 2 hours at 20° C., the precipitate formed is filtered off and washed twice with diisopropyl ether (40 cc in total). The filtrate is concentrated to dryness under reduced pressure (20 mm Hg) at 50° C. Succinimide 2-n-pentyl-3-hydroxynonanoate (42.6 g) is thus obtained in the form of a yellow oil.

2-n-Pentyl-3-hydroxynonanoic acid can be prepared in accordance with the method of E. Lederer et al., Bull. Soc. Chim., 1952, 413.

EXAMPLE 19

A chloromethylated styrene/divinylbenzene copolymer (98/2) (12.5 g) containing 1.2 milliequivalents of chlorine per gram is added to a solution of benzyl N-t-butoxycarbonyl-α-D-glutamate (6.07 g) in ethanol (70 cc). The reaction mixture is stirred for ¼ hour at 28° C. Triethylamine (2.25 cc) is then added and the reaction mixture is stirred for 65 hours at 78° C. The polymer is filtered off, washed successively 3 times with ethanol (300 cc in total) and 3 times with methylene chloride (300 cc in total) and then dried under reduced pressure (20 mm Hg) at 40° C. This yields $O^1$-benzyl-N-t-butoxycarbonyl-D-glutamyl-polymer (17 g). Alanine is condensed with the $O^1$-benzyl-N-t-butoxycarbonyl-D-glutamyl-polymer by carrying out the following series of operations in a reactor fitted with a stirrer and, at its base, with a fritted glass filter.

(1) The polymer is washed in 3 successive stages with methylene chloride (3×100 cc). Each addition of solvent is followed by stirring for 3 minutes and then by draining.

(2) The t-butoxycarbonyl protective group of the glutamic acid is then removed by adding a mixture of trifluoroacetic acid and methylene chloride (1/1 by volume) (100 cc), then stirring for 20 minutes and finally draining.

(3) The resin is then washed successively with:
 (a) methylene chloride (3×100 cc),
 (b) methanol (3×100 cc) and
 (c) methylene chloride (3×100 cc),
each addition of solvent being followed by stirring for 3 minutes and by draining.

(4) The polymer is then neutralised by adding a mixture of methylene chloride and N-methylmorpholine (9/1 by volume) (100 cc), stirring for 10 minutes and then draining.

(5) The resin is then washed with methylene chloride (3×100 cc), each addition of solvent being followed by stirring for 3 minutes and by draining.

(6) The following are then added in succession:
 (a) a solution of N-t-butoxycarbonyl-L-alanine (3.78 g) in methylene chloride (50 cc), with stirring for 10 minutes, and
 (b) a solution of dicyclohexylcarbodiimide (4.13 g) in methylene chloride (50 cc), with stirring for 20 hours and draining.

(7) The resin is washed successively with:
 (a) methylene chloride (3×100 cc),
 (b) acetic acid (3×100 cc) and
 (c) methylene chloride (3×100 cc)
each addition of solvent being followed by stirring for 3 minutes and by draining.

This yields $O^1$-benzyl-N-(t-butoxycarbonyl-L-alanyl)-D-glutamyl-polymer.

Heptadecanoic acid is condensed with the dipeptide-polymer by repeating operations 1, 2, 3, 4, 5, 6 and 7. Operation no. 6 is modified as follows:

The following are added in succession:
 (a) a solution of heptadecanoic acid (5.4 g) in methylene chloride (50 cc), with stirring for 10 minutes, and
 (b) a solution of dicyclohexylcarbodiimide (4.13 g) in methylene chloride (50 cc), with stirring for 20 hours and draining.

This yields $O^1$-benzyl-N-(N-heptadecanoyl-L-alanyl)-D-glutamyl-polymer.

This polymer is suspended in trifluoroacetic acid (100 cc) contained in a reactor fitted with a stirrer and, at its base, with a fritted glass filter. A stream of hydrogen bromide is passed through this suspension for 90 minutes. The resin is then drained and washed 3 times with acetic acid (300 cc in total), each addition of acetic acid being followed by stirring for 3 minutes and by draining. The filtrates are combined and concentrated to dryness under reduced pressure (20 mm Hg) at 50° C.

The residue thus obtained is suspended in ethyl acetate (30 cc), filtered off, washed twice with ether (60 cc in total) and dried. This yields a solid (1.97 g) which is chromatographed on a column of diameter 2.2 cm, containing neutral silica gel (0.04–0.063 mm) (40 g).

Elution is carried out successively with a mixture of cyclohexane and ethyl acetate (1/1 by volume) (350 cc), ethyl acetate (400 cc), a mixture of ethyl acetate and acetic acid (95/5 by volume) (700 cc), a mixture of ethyl acetate and acetic acid (90/10 by volume) (950 cc), a mixture of ethyl acetate and acetic acid (80/20 by volume) (750 cc) and acetic acid (1.6 liters), 50 cc fractions being collected. Fractions 65 to 94 are combined and concentrated to dryness under reduced pressure (20 mm Hg) at 50° C. This yields N-heptadecanoyl-L-alanyl-D-glutamic acid (0.88 g).

Rf=0.61 [silica gel; n-butanol/pyridine/acetic acid/water (50/20/6/24 by volume)]

Analysis: calculated %: C 63.80, H 9.85, N 5.95: found %: 60.1, 9.3, 5.8: sulphuric ash: 5.6%.

The present invention includes within its scope pharmaceutical compositions which comprise at least one dipeptide of formula II or non-toxic salt thereof, in association with one or more compatible and pharmaceutically acceptable carriers, diluents or adjuvants. These compositions can be used either as vaccine adjuvants or as non-specific stimulants of anti-infectious and antitumoral immunity.

When used as vaccine adjuvants, the compounds according to the invention are administered at the same time and by the same method as the antigen (viral, bacterial, parasitic or other antigen) against which it is desired to increase the cell immunity reactions (delayed-type hypersensitivity) or the production of circulating or local antibodies in the immunised subject (man or domestic animal).

The products are administered in relatively low doses (of the order of one mg) as a mixture with the antigen and by the same method (e.g. by the intramuscular, subcutaneous, intravenous, intranasal or oral method). If necessary, the compound according to the invention and the antigen can be emulsified in an appropriate oily excipient or incorporated into liposomes.

As non-specific immunostimulants, the compounds of the invention are administered in doses of from 0.1 to 50 mg/kg animal body weight by the parenteral method (intravenous, subcutaneous or intramuscular method) or by the intranasal, oral, rectal or, if appropriate, intratumoral method.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting, sweetening and flavouring agents.

Preparations according to the invention for parenteral administration include sterile aqueous solutions, suspensions and emulsions. Examples of non-aqueous vehicles are propylene glycol, polyethylene glycol, vegetable oils such as olive oil, and injectable organic esters such as ethyl oleate. These compositions may also contain adjuvants, in particular wetting agents, emulsifiers or dispersing agents. They may be sterilised by, for example, filtration through a bacteria-retaining filter, by incorporation in the compositions of sterilising agents, or by heating. They may also be manufactured in the form of solid compositions sterilised, e.g. by irradiation, which can be dissolved in sterile water or dispersed in any other sterile injectable medium before use.

Compositions for intranasal administration may be sterile aqueous solutions, suspensions or emulsions, which may if necessary be associated with a compatible propellant.

Compositions for rectal administration are suppositories which contain, in addition to the active substance, excipients such as cacao butter or a suitable wax base.

The following Examples illustrate pharmaceutical compositions according to the invention:

EXAMPLE 20

A solution which can be administered intravenously and has the following composition is prepared in accordance with the usual technique:

| | |
|---|---|
| Benzyl N—lauroyl-L-alanyl-α-D-glutamate | 0.5 g |
| injectable solution | 5 cc |

EXAMPLE 21

A solution which can be administered intravenously and has the following composition is prepared in accordance with the usual technique:

| | |
|---|---|
| N—Palmitoyl-L-alanyl-α-D-glutamic acid | 0.5 g |
| injectable solution | 5 cc |

We claim:
1. A dipeptide of the formula:

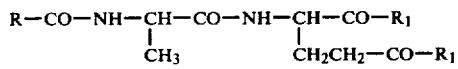

in which R-CO represents a fatty acid residue and the symbols $R_1$, which are identical or different, represent a hydroxyl or amino radical or an alkoxy radical of 1 to 4 carbon atoms, which is unsubstituted or substituted by a phenyl or nitrophenyl radical, the alanine residue being in the L form and the residue of glutamic acid or derivative thereof being in the D form, and the metal salts and addition salts with nitrogen-containing bases of the said dipeptide.

2. A dipeptide according to claim 1, wherein R represents a hydrogen atom, an alkyl radical of 1 to 44 carbon atoms, which is unsubstituted or substituted by a hydroxyl, phenyl or cyclohexyl radical or an alkenyl radical of 2 to 29 carbon atoms containing one or more double bonds, or R-CO represents a mycolic acid residue.

3. A dipeptide according to claim 1 in which R is alkyl of 1 to 23 carbon atoms or alkenyl of 2 to 23 carbon atoms containing one to four double bonds, the said alkyl or alkenyl being unsubstituted or substituted by hydroxyl, phenyl or cyclohexyl, such that R contains at least seven but not more than 29 carbon atoms, one of the radicals $R_1$ represents hydroxy or amino and the other represents hydroxy, amino or benzyloxy.

4. A dipeptide according to claim 1 in which R-CO is an alkanoyl or alkenoyl radical of 8 to 20 carbon atoms and $R_1$ represents hydroxy, amino or benzyloxy.

5. Benzyl N-lauroyl-L-alanyl-α-D-glutamate.
6. Benzyl N-lauroyl-L-alanyl-D-glutaminate.
7. N-Lauroyl-L-alanyl-D-glutamine.
8. N-Lauroyl-L-alanyl-D-glutamic acid.
9. Benzyl N-lauroyl-L-alanyl-D-isoglutaminate.
10. N-Lauroyl-L-alanyl-D-isoglutamine.
11. N-Lauroyl-L-alanyl-D-glutamamide.
12. Benzyl N-(5-phenylvaleryl)-L-alanyl-α-D-glutamate.
13. N-(5-Phenylvaleryl)-L-alanyl-D-glutamic acid.
14. Benzyl N-octanoyl-L-alanyl-α-D-glutamate.
15. Benzyl N-palmitoyl-L-alanyl-α-D-glutamate.
16. N-Arachidonoyl-L-alanyl-D-glutamic acid.
17. N-Palmitoyl-L-alanyl-D-glutamic acid.
18. Benzyl N-docosanoyl-L-alanyl-α-D-glutamate.
19. Benzyl N-(3-cyclohexylpropionyl)-L-alanyl-α-D-glutamate.
20. Benzyl N-(3,5,5-trimethylhexanoyl)-L-alanyl-α-D-glutamate.
21. Benzyl N-(2-n-pentyl-3-hydroxynonanoyl)-L-alanyl-α-D-glutamate.
22. N-Heptadecanoyl-L-alanyl-D-glutamic acid.
23. A pharmaceutical composition for use as a vaccine adjuvant or immunostimulant which comprises an effective amount of a dipeptide according to claim 1 or a non-toxic salt thereof in association with one or more compatible, pharmaceutically acceptable carriers, diluents or adjuvants.
24. Method of stimulating the immune reactions in man or a domestic animal which comprises administering thereto an effective amount of a dipeptide as claimed in claim 1.

* * * * *